United States Patent
Storz

(10) Patent No.: US 6,245,086 B1
(45) Date of Patent: *Jun. 12, 2001

(54) MOTOR-DRIVEN MEDICAL INSTRUMENT WITH FLEXIBLE SHAFT

(75) Inventor: Karl Storz, deceased, late of Tuttlingen (DE), by Sybil Storz-Reling, Executor

(73) Assignee: Karl Storz GmbH & Co., KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/011,865

(22) PCT Filed: Aug. 19, 1996

(86) PCT No.: PCT/DE96/01537

§ 371 Date: Feb. 17, 1998

§ 102(e) Date: Feb. 17, 1998

(87) PCT Pub. No.: WO97/06736

PCT Pub. Date: Feb. 27, 1997

(30) Foreign Application Priority Data

Aug. 18, 1995 (DE) .............................. 195 30 478

(51) Int. Cl.[7] .................................................. A61B 17/14
(52) U.S. Cl. .............................................................. 606/180
(58) Field of Search ..................................... 606/180, 181, 606/182, 171, 170, 167, 169; 433/91; 408/141; 464/106, 52, 57; 403/90, 230, 74, 57, 229; 128/122.1; 74/500.5

(56) References Cited

U.S. PATENT DOCUMENTS

| | | | | |
|---|---|---|---|---|
| 1,984,663 | * | 12/1934 | Tatham ................................. | 606/180 |
| 2,030,511 | * | 2/1936 | Gruber ................................. | 646/117 |
| 2,911,660 | * | 11/1959 | Klemas et al. ....................... | 606/180 |
| 3,847,154 | * | 11/1974 | Nordin ................................. | 606/180 |
| 4,071,029 | * | 1/1978 | Richmond et al. .................. | 606/180 |
| 4,646,738 | * | 3/1987 | Trott .................................... | 606/180 |
| 5,286,253 | * | 2/1994 | Fucci .................................... | 606/180 |
| 5,320,635 | * | 6/1994 | Smith ................................... | 606/180 |
| 5,411,514 | * | 5/1995 | Fucci et al. .......................... | 606/180 |
| 5,628,763 | * | 5/1997 | Yazawa et al. ...................... | 606/180 |
| 5,782,836 | * | 7/1998 | Umber et al. ....................... | 606/180 |

FOREIGN PATENT DOCUMENTS

| | | | | |
|---|---|---|---|---|
| 494022 | * | 9/1970 | (DE) ..................................... | 606/180 |
| 3536747 | * | 4/1996 | (DE) ..................................... | 646/117 |
| 2681919 | * | 9/1991 | (FR) ..................................... | 646/117 |

* cited by examiner

Primary Examiner—Henry J. Recla
Assistant Examiner—Tan-Uyen Thi Ho
(74) Attorney, Agent, or Firm—St. Onge Steward Johnston & Reens LLC

(57) ABSTRACT

Disclosed is a medical instrument having at least one surgical element, such as a knife or the like disposed at the distal end thereof, a motor disposed at the proximal end thereof, and a shaft which connects the shaft of the motor to the shaft of the surgical instrument in such a manner that the surgical element is rotated.

According to the invention either the motor is detachably connected to said shaft of the said surgical element in an as such known manner so that a bend can be inserted between the motor shaft and said shaft disposed in the instrument or that a flexible bend is inserted between the motor and the shaft in such a manner that the motor shaft and the shaft disposed in the instrument includes an adjustable angle.

7 Claims, 1 Drawing Sheet

MOTOR-DRIVEN MEDICAL INSTRUMENT WITH FLEXIBLE SHAFT

TECHNICAL FIELD

The present invention relates to a medical instrument as set forth in the generic part of the alternative independent claims 1 and 2.

Medical instruments of the class presupposed in the generic part of the alternative independent claims 1 and 2 are employed, by way of illustration, in the form of a so-called sheaver. Instruments of this type have a motor disposed at their proximal ends. The driven shaft of this motor is connected via a transmission shaft disposed in the instrument or connected directly to at least one surgical element, such as a knife, an ablating element or the like, disposed at the distal end.

STATE OF THE ART

The known generic instruments are either designed in such a manner that the engine is disposed coaxially to the shaft in the instrument or that the motor driven shaft and the shaft in the instrument include a specific, predetermined, unchangeable angle. Usually the motor is disposed in a hand piece with which the physician holds the instrument.

Which of the possible arrangements is preferable depends on the personal preferences of the person operating the instrument as well as on the respective procedure to be executed.

Therefore, in the past two instruments, one in which the hand piece is disposed at an angle to the instruments and one in which the hand piece and the instrument are disposed coaxially, were purchased, making the investment rather expensive.

DESCRIPTION OF THE INVENTION

The object of the present invention is to improve a generic type medical instrument in such a manner that the cost of the investment is reduced.

An invented solution to this object is set forth in the alternative independent claims 1 and 2.

In the solution set forth in claim 1, the motor is connected in an as such known detachable manner to the shaft. A bend can be inserted between the motor shaft and the shaft disposed in the instrument.

In this way, the motor can be flanged both coaxially to the instrument and by means of the bend to the instrument in such manner that it is connected at an angle.

In the solution set forth in claim 2, a flexible bend is inserted between the motor and the shaft. By adjusting this bend, the motor can be disposed coaxially to the shaft as well as at any desired angle.

Claim 3 characterizes that the motor is disposed in an as such known manner in a hand piece of the instrument, thereby improving the instrument egonomically, because the operating person can hold the instrument by the hand piece.

The power transmission between the motor shaft and the transmission shaft in the instrument can occur, in principle, in any manner, by way of illustration via a deflection transmission.

The improvement described in claim 4, in which the power transmission occurs via a flexible shaft, has the advantage that it is not only simple and inexpensive to realize, but it also permits adjusting the angle between the motor driven shaft and the transmission shaft in a simple manner.

By means of the improvement described in claim 5 length compensation is achieved for the different constructions of the motor and of the instrument:

For this purpose, the one end of a first rotatable helical spring is attached to a holder for the motor driven shaft and the other end to a rotatably borne connecting element. The rotatably borne connecting element is connected via the flexible shaft or the cardan joint to a holder for the shaft of the surgical element.

For medical instruments, it is important that the instrument can be dismantled for cleaning and sterilizing. The improvement set forth in claim 6 simplifies reassembly of the instrument following dismantling: for this purpose a second stationary helical spring is provided which surrounds the cardan joint and presses a bearing element, which is attached distally to the cardan joint, into a cone.

Claim 7 describes an embodiment in which two angles, by way of illustration 0° and 90°, can be adjusted in an extremely simple manner:

According to this improvement, a two-part housing is provided, the two housing halves can be rotated toward each other in order to set the angle between the motor driven shaft and the drive shaft of the surgical instrument.

BRIEF DESCRIPTION OF THE DRAWING

The present invention is made more apparent in the following using a preferred embodiment with reference to the drawing, depicting FIG. 1 a preferred embodiment of a bend, FIG. 2 the bend depicted in FIG. 1 in an extended state without any housing,

DESCRIPTION OF THE PREFERRED EMBODIMENT

Figure 1:
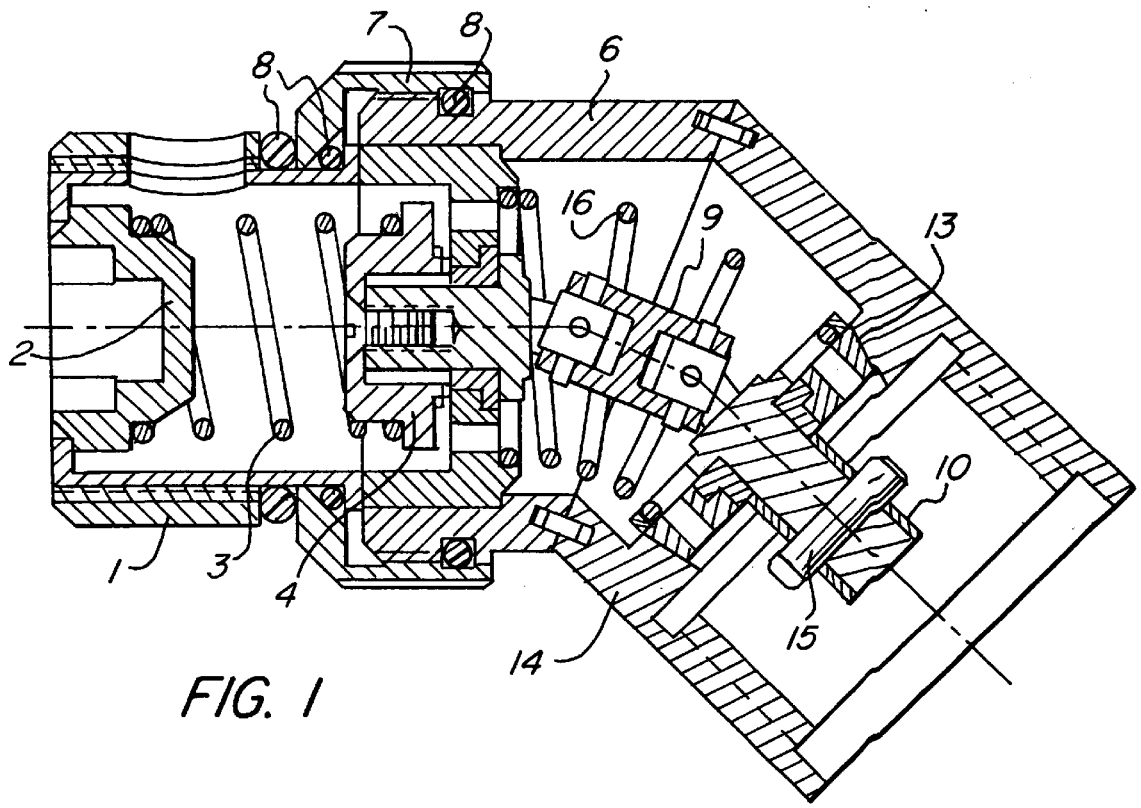
Figure 2:
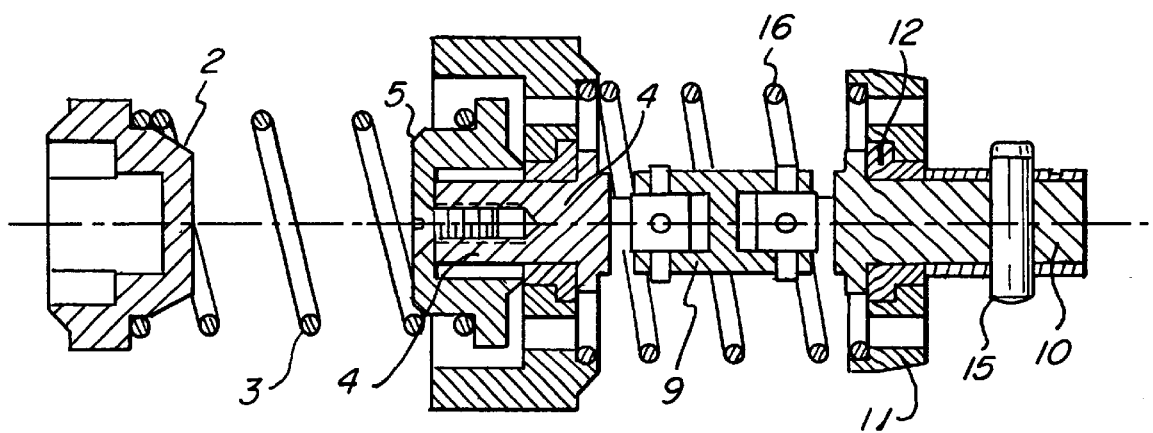

Only the bend is depicted in FIGS. 1 and 2. The surgical instrument, such as a knife or the like, disposed at the distal end of the invented instrument and the motor disposed at the proximal end are designed in an as such known manner, for this reference is made, by way of illustration to the sheaver from Karl Storz GmbH & Co, Tuttlingen, Del., thus obviating a description of this part.

The bend depicted in FIGS. 1 and 2 is provided in a base part 1 of the housing with a rotatably borne holder 2 for the not depicted motor driven shaft. The holder 2 is connected via a rotatable helical spring 3 to a connecting element 4 in such a manner that a rotating movement of the driven shaft of the motor is transmitted to the connecting element. The purpose of the helical spring 3 is only to compensate length, which is necessary due to the different constructions of the motor part and of the surgical element. 5 stands for a fastening screw.

The connecting element 4 is rotatably borne in the one half 6 of a two-part housing. The two-part housing is connected via a union nut 7 to the base part 1. O-rings 8 seal off the housing fluid tight from the surroundings. In this manner, the parts can be easily dismantled for cleaning.

Linked on the distal side of the rotatably borne connecting element 4 is one side of a cardan joint 9, whose other side is connected to a holder 10 for the shaft of the surgical element, not depicted. The holder 10 is rotatably borne via a slide bearing 12 in a bearing element 11, which is inserted by means of a cone 13 into the second part 14 of the two-part housing. 15 stands for a pin which serves as a locking piston between the holder 10 and the shaft of the surgical element.

A second stationary helical spring 16 surrounds the caradan joint 9 and presses the bearing element 11 into the holder cone on the second part 14 of the two-part housing.

In the depicted preferred embodiment, the two hosing halves 6 and 14 are firmly connected to each other. However, the two housing halves can be set rotatably in order to adjust the angle between the motor driven shaft and the drive shaft of the surgical element. In this way,, by way of illustration, the angles 0° and 45° can be set.

In the preceding, the present invention is made more apparent using a preferred embodiment with reference to the drawing to which reference is explicitly to be made for the explanation of all details not explained in more detail.

What is claimed is:

1. A universal connector for medical instrument, comprising:
   a housing having at least two housing parts rotatable relative to one another, said housing having a proximal end adapted to receive a motor shaft, which is rotated about an axis and selected from the group consisting of a plurality of motor shafts having various axial dimensions, and a distal end adapted to receive an instrument shaft; and
   a torque transmission mechanism in said housing for transmitting a torque generated by said motor shaft to the instrument shaft, said torque transmitting mechanism comprising:
      a first seat mounted to the proximal end of the housing and adapted to be detachably connected to the motor shaft to rotate therewith;
      a connecting element rotatably mounted between the proximal and distal ends,
      a flexible shaft rotatably coupled to the connecting element at one end and adapted to couple to the instrument shaft at another end, and
      a first helical spring braced against and rotatably coupling the first seat and the connecting element, said first seat being axially displaceable in the housing against a force generated by the first helical spring to allow for variable axial dimensions of the motor shaft.

2. The universal connector for medical instruments defined in claim 1 wherein the housing parts rotate between a first position, wherein these parts are aligned with one another, so that the motor and instrument shafts extend coaxially, and a plurality of second positions, in each of which the motor and instrument shaft extend at a variable angle with respect to one another.

3. The universal connector for medical instruments defined in claim 1 wherein the torque transmission mechanism further includes a second seat rotatably mounted to the distal end of the housing to rotatably interconnect the flexible shaft and the instrument shaft, the universal connector for medical instruments further comprising a holder at the distal end said second seat adapted to couple to the instrument shaft adapted to be detachably connected to the instrument shaft.

4. The universal connector for medical instruments defined in claim 3 wherein the distal end of the housing is formed with an annular piece tapering towards the holder and receiving a bearing element surrounding the second seat, the universal connector for medical instruments further comprising a second stationary helical spring urging the bearing element into the annular piece.

5. The universal connector for medical instruments defined in claim 1 wherein the connecting element includes first and second parts detachable from one another so as to dismantle said medical instrument for clearing and sterilizing.

6. The universal connector for medical instruments defined in claim 3 further comprising a pin displaceable transversely to the axis of rotation to connect the second seat to the instrument shaft.

7. The universal connector for medical instruments defined in claim 1 wherein the flexible shaft includes at least one cardan joint.

* * * * *